United States Patent
Marsden et al.

(10) Patent No.: US 9,849,229 B2
(45) Date of Patent: Dec. 26, 2017

(54) SPLIT-TIP CATHETER

(71) Applicant: Covidien LP, Mansfield, MA (US)

(72) Inventors: Brent Marsden, Reading, MA (US); Michael R. Sansoucy, Wrentham, MA (US); Richard M. Braga, North Easton, MA (US)

(73) Assignee: COVIDIEN LP, Mansfield, MA (US)

( * ) Notice: Subject to any disclaimer, the term of this patent is extended or adjusted under 35 U.S.C. 154(b) by 133 days.

(21) Appl. No.: 14/261,461

(22) Filed: Apr. 25, 2014

(65) Prior Publication Data
US 2015/0306302 A1   Oct. 29, 2015

(51) Int. Cl.
- A61M 31/00   (2006.01)
- A61M 37/00   (2006.01)
- A61M 1/36    (2006.01)
- A61M 25/00   (2006.01)
- A61M 25/06   (2006.01)

(52) U.S. Cl.
CPC ........ A61M 1/3661 (2014.02); A61M 25/003 (2013.01); A61M 25/0074 (2013.01); A61M 25/007 (2013.01); A61M 2025/0031 (2013.01); A61M 2025/0681 (2013.01)

(58) Field of Classification Search
CPC ............ A61M 1/3661; A61M 25/0147; A61M 25/0068; A61M 25/0026
USPC ...................................................... 604/95.04
See application file for complete search history.

(56) References Cited

U.S. PATENT DOCUMENTS

| | | |
|---|---|---|
| 4,309,994 A | 1/1982 | Grunwald |
| 4,925,452 A | 5/1990 | Melinyshyn et al. |
| 5,197,976 A | 3/1993 | Herweck et al. |
| 5,254,084 A | 10/1993 | Geary |
| 5,273,534 A | 12/1993 | Knoepfler |
| 5,279,599 A * | 1/1994 | Wilk ...................... A61M 1/008 604/313 |
| 5,322,519 A * | 6/1994 | Ash ........................ A61M 1/284 604/264 |
| 5,476,453 A | 12/1995 | Mehta |
| 5,599,304 A | 2/1997 | Shaari |
| 5,624,413 A | 4/1997 | Markel et al. |
| 5,695,457 A | 12/1997 | St. Goar et al. |
| 5,704,915 A | 1/1998 | Melsky et al. |
| 5,718,692 A | 2/1998 | Schon et al. |
| 5,776,111 A | 7/1998 | Tesio |
| 5,800,414 A | 9/1998 | Cazal |
| 5,807,311 A | 9/1998 | Palestrant |
| 5,947,953 A | 9/1999 | Ash et al. |
| 5,957,912 A | 9/1999 | Heitzmann |

(Continued)

Primary Examiner — Edelmira Bosques (57) ABSTRACT

A catheter includes an elongate shaft having proximal and distal end portions defining a longitudinal axis, and first and second tip segments. The elongate shaft and the first and second tip segments define respective first and second lumens. Each tip segment includes a proximal portion fixed relative to the distal end of the elongate shaft, and a distal portion. Each tip segment defines a side opening in fluid communication with a respective one of the first and second lumens. Each tip segment is movable between a straight configuration in which each respective tip segment is substantially parallel to the longitudinal axis, and a curved configuration in which each tip segment has a concave portion with respect to the longitudinal axis. The side openings face each other along the concave portions.

20 Claims, 4 Drawing Sheets

(56) References Cited

U.S. PATENT DOCUMENTS

| | | |
|---|---|---|
| 5,964,796 A | 10/1999 | Imran |
| 6,001,079 A | 12/1999 | Pourchez |
| 6,074,374 A | 6/2000 | Fulton |
| 6,117,117 A | 9/2000 | Mauch |
| 6,156,016 A | 12/2000 | Maginot |
| 6,190,349 B1 | 2/2001 | Ash et al. |
| 6,475,207 B1 | 11/2002 | Maginot et al. |
| 6,482,169 B1 | 11/2002 | Kuhle |
| 6,513,527 B1 | 2/2003 | Abdel-Aziz |
| 6,558,356 B2 | 5/2003 | Barbut |
| 6,585,705 B1 | 7/2003 | Maginot et al. |
| 6,638,242 B2 | 10/2003 | Wilson et al. |
| 6,659,134 B2 | 12/2003 | Navis |
| 6,682,519 B1 | 1/2004 | Schon |
| 6,695,832 B2 | 2/2004 | Schon et al. |
| 6,719,749 B1 | 4/2004 | Schweikert et al. |
| 6,723,084 B1 | 4/2004 | Maginot et al. |
| 6,743,218 B2 | 6/2004 | Maginot et al. |
| 6,758,836 B2 | 7/2004 | Zawacki |
| 6,872,198 B1 | 3/2005 | Wilson et al. |
| 6,881,211 B2 | 4/2005 | Schweikert et al. |
| 6,913,601 B2 | 7/2005 | St. Goar et al. |
| 6,916,313 B2 | 7/2005 | Cunningham |
| 6,921,396 B1 | 7/2005 | Wilson et al. |
| 6,966,886 B2 | 11/2005 | Appling |
| 6,997,894 B2 | 2/2006 | Caresio |
| 7,008,412 B2 | 3/2006 | Maginot |
| 7,013,928 B2 | 3/2006 | Navis |
| 7,018,374 B2 | 3/2006 | Schon et al. |
| RE39,451 E | 12/2006 | Kuhle |
| D550,839 S | 9/2007 | Zawacki et al. |
| 7,300,430 B2 | 11/2007 | Wilson et al. |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,465,286 B2 | 12/2008 | Patterson et al. |
| 7,575,563 B2 | 8/2009 | Appling |
| RE40,913 E | 9/2009 | Schweikert et al. |
| D603,044 S | 10/2009 | Appling et al. |
| 7,740,780 B2 | 6/2010 | Hamboly |
| 7,749,185 B2 | 7/2010 | Wilson et al. |
| 7,806,889 B2 | 10/2010 | Raulerson et al. |
| 7,833,214 B2 | 11/2010 | Wilson et al. |
| 7,875,019 B2 | 1/2011 | Barron et al. |
| 7,918,817 B2 | 4/2011 | Schon et al. |
| 7,943,077 B2 | 5/2011 | Sansoucy |
| 7,972,465 B2 | 7/2011 | Patterson et al. |
| 7,981,093 B2 | 7/2011 | Schon et al. |
| 8,021,321 B2 | 9/2011 | Zawacki |
| 8,029,457 B2 | 10/2011 | Ash et al. |
| 8,057,460 B2 | 11/2011 | Hobbs et al. |
| 8,152,951 B2 | 4/2012 | Zawacki et al. |
| 8,246,600 B2 | 8/2012 | Raulerson et al. |
| 8,257,635 B2 | 9/2012 | Sansoucy |
| 8,394,218 B2 | 3/2013 | Sansoucy |
| 8,430,988 B2 | 4/2013 | Patterson et al. |
| 8,500,939 B2 | 8/2013 | Nimkar et al. |
| 8,585,950 B2 | 11/2013 | Appling et al. |
| 8,608,995 B2 | 12/2013 | Sansoucy |
| 2002/0099326 A1 | 7/2002 | Wilson et al. |
| 2003/0088213 A1 | 5/2003 | Schweikert et al. |
| 2004/0171997 A1 | 9/2004 | Wilson et al. |
| 2004/0243095 A1 | 12/2004 | Nimkar et al. |
| 2005/0054990 A1 | 3/2005 | Graft et al. |
| 2005/0059925 A1 | 3/2005 | Maginot et al. |
| 2005/0171469 A1 | 8/2005 | Cunningham |
| 2005/0187535 A1 | 8/2005 | Wilson et al. |
| 2005/0197624 A1 | 9/2005 | Goodson et al. |
| 2005/0277862 A1 | 12/2005 | Anand |
| 2005/0283111 A1 | 12/2005 | Maurice |
| 2006/0009801 A1* | 1/2006 | McGurk .......... A61B 17/00491 606/214 |
| 2007/0078438 A1 | 4/2007 | Okada |
| 2007/0233042 A1 | 10/2007 | Moehle et al. |
| 2008/0009803 A1 | 1/2008 | Schon et al. |
| 2008/0039774 A1 | 2/2008 | Zawacki et al. |
| 2008/0171989 A1* | 7/2008 | Bell ................. A61M 25/0662 604/170.02 |
| 2008/0214980 A1 | 9/2008 | Anand |
| 2009/0192435 A1* | 7/2009 | Gregersen .......... A61M 1/3653 604/6.16 |
| 2012/0232570 A1* | 9/2012 | Jenson .............. A61B 17/3207 606/159 |
| 2014/0012209 A1 | 1/2014 | Sansoucy |
| 2014/0018772 A1* | 1/2014 | Ash ................... A61M 25/0043 604/508 |

* cited by examiner

SPLIT-TIP CATHETER

BACKGROUND

Catheters are flexible medical instruments that facilitate withdrawal and introduction of fluids from and to body cavities, ducts, and vessels. Catheters can be used, for example, in hemodialysis procedures. During some hemodialysis procedures, a multiple lumen catheter having an arterial lumen and a venous lumen is inserted into a subject's body. Blood is withdrawn through the arterial lumen of the catheter, and the removed blood is directed to a hemodialysis machine that dialyzes the blood to remove waste and toxins. The dialyzed blood is then returned to the body through a venous lumen of the catheter.

Some hemodialysis catheters include a staggered tip design in which an arterial inlet is upstream of a venous outlet to increase the likelihood that blood returning to a subject through the venous outlet will be expelled downstream from the arterial inlet. In use, such staggered tip hemodialysis catheters can become occluded as a result of fibrin sheath formation, thrombus formation, and/or the position of the hemodialysis catheter relative to a vessel wall (positional occlusion). Poor flow resulting from these conditions can limit the efficiency and/or effectiveness in delivering dialysis treatment to a subject. Common measures used to resolve occlusion of staggered tip hemodialysis catheters include reversing the blood lines of the catheter to the hemodialysis machine. While often effective in reestablishing flow, reversing the blood lines of a staggered tip catheter can itself adversely impact efficiency of the hemodialysis treatment as a result of expulsion of cleaned blood upstream of the point of intake of blood to be treated. Upstream expulsion of cleaned blood increases the potential for clean blood to be drawn back into the catheter, a condition referred to as recirculation, which decreases efficiency of dialysis by increasing treatment time to reach prescribed blood cleanliness levels.

SUMMARY

The present disclosure is directed to split-tip catheters having movable, opposed catheter tip segments that reduce the likelihood of recirculation and/or occlusion during medical procedures (e.g., hemodialysis).

In one aspect of the present disclosure, a catheter includes an elongate shaft and first and second tip segments. The elongate shaft has a proximal end portion and a distal end portion, the proximal and distal end portions defining a longitudinal axis. The elongate shaft and the first and second tip segments define respective first and second lumens. Each tip segment has a proximal portion and a distal portion, the proximal portion of each tip segment fixed relative to the distal end portion of the elongate shaft. Each tip segment defines a side opening in fluid communication with a respective one of the first and second lumens. Each tip segment is movable between a straight configuration and a curved configuration. In the straight configuration, each tip segment is substantially parallel to the longitudinal axis. In the curved configuration, each tip segment has a concave portion with respect to the longitudinal axis and the side openings face each other along the concave portions.

In certain embodiments, the distal portion of the first tip segment is adjacent the distal portion of the second tip segment in the straight configuration and in the curved configuration.

In some embodiments, the distal portions of the first and second tip segments define respective tip openings in fluid communication with a respective one of the first and second lumens. Each tip opening may define a cross-sectional area substantially similar in size to a cross-sectional area transverse to a flow path of a respective one of the first and second lumens. Additionally or alternatively, each tip opening may define a cross-sectional area substantially similar in size to a cross-sectional area defined by the respective side opening of the respective tip segment.

In certain embodiments, in the curved configuration, the distance between the side opening of the respective tip opening is at least about half the length of the respective tip segment. Additionally or alternatively, the side opening defined by the first tip segment may be about 1 cm to about 4 cm from the respective tip opening defined by the first tip segment, and the side opening defined by the second tip segment may be about 1 cm to about 4 cm from the respective tip opening defined by the second tip segment.

In some embodiments, the distal portions of the first and second tip segments are coterminous with one another in both the straight and curved configurations. Additionally or alternatively, the first tip and second tip segments may each have a length of about 1 cm to about 4 cm.

In certain embodiments, in the curved configuration, the maximum lateral distance between outer surfaces of the first and second tip segments is from about 25 mm to about 30 mm.

In some embodiments, the first and second tip segments each have a D-shaped outer surface with a flat side of the D-shaped outer surface of each tip segment facing the flat side of the D-shaped outer surface of the other tip segment, and the side opening of each tip segment is defined along the flat side of the D-shaped outer surface of the respective tip segment.

In certain embodiments, the first and second tip segments are symmetrical to one another, in both the straight and curved configurations, about at least one plane bisecting the elongate shaft and including the longitudinal axis.

In some embodiments, the first and second lumens have a D-shaped cross-section from the proximal end portion of the elongate shaft to the distal portion of each respective tip segment.

In certain embodiments, the elongate shaft includes a septum disposed between the first and second lumens from the proximal end portion to the distal end portion of the elongate shaft.

In some embodiments, each of the side openings defines an open area substantially similar in size to a cross-sectional area transverse to a flow path of a respective one of the first and second lumens.

In certain embodiments, the first and second tip segments are biased toward the curved configuration.

In some embodiments, the catheter further includes a wire parallel to the longitudinal axis and coupled to the distal portions of the first and second tip segments. The wire is movable in the direction of the longitudinal axis to move the first and second tip segments between the straight and curved configurations. In some embodiments, the wire is movable toward the proximal end portion of the elongate shaft to move the first and second tip segments from the straight configuration to the curved configuration. The elongate shaft may define a third lumen and the wire may be at least partially disposed in the third lumen. Additionally or alternatively, the catheter may further include a collar disposed along the wire and movable to lock the wire in place.

Embodiments can include one or more of the following advantages.

In some embodiments, the first and second tip segments of the catheter are movable into a curved configuration in which side openings face each other along the concave portions of the first and second tip segments. In this orientation, the side openings face away from a vessel or body cavity wall. Thus, as compared to other orientations of openings, the facing side openings are less likely to become occluded by the vessel or body cavity wall. This can reduce the likelihood that positional occlusion will interrupt a medical treatment of a subject.

In certain embodiments, the distal portions of the first and second tip segments define respective tip openings in fluid communication with a respective one of the first and second lumens. The resulting flow of blood through the catheter can result in an effectively staggered flow in which blood moves into the catheter through a side opening and exits the catheter through an opposite tip opening. This separation of inlet and exhaust flows can reduce the likelihood that treated blood exiting the tip opening would be recirculated back into the catheter through one of the side openings. Additionally or alternatively, the presence of a tip opening and a side opening in fluid communication with each respective lumen provides redundancy that reduces the likelihood that occlusion of one opening would interrupt a medical treatment of a subject. For example, if one of the side openings becomes occluded, flow can move into the respective lumen through the respective tip opening until the occlusion can be cleared.

In certain embodiments, the first and second tip segments are symmetrical to one another, in both the straight and curved configurations, about at least one plane bisecting the elongate shaft and including the longitudinal axis. This symmetry can facilitate reversing the flow through the catheter while having little to no impact on the amount of blood recirculated into the catheter (e.g., the amount of blood recirculated into the catheter in either flow direction can be substantially the same).

Other aspects, features, and advantages will be apparent from the description, drawings, and the claims.

BRIEF DESCRIPTION OF THE DRAWINGS

Corresponding reference characters indicate corresponding parts throughout the drawings.

DETAILED DESCRIPTION

In this disclosure, the term "proximal" refers to the portion of a structure closer to a clinician, while the term "distal" refers to the portion of the same structure further from the clinician. As used herein, the term "subject" refers to a human patient or other animal. The term "clinician" refers to a doctor, nurse, or other care provider and may include support personnel. The terms "generally," "substantially," and "about" shall be understood as words of approximation that take into account relatively little to no variation in the modified term(s) (e.g., differing by less than 2%).

Referring now to FIGS. 1-5, a catheter 100 includes an elongate shaft 110, first and second tip segments 130, 150 distally extending from the elongate shaft 110 and, optionally, a catheter hub 170 and an extension tube assembly 180 proximally extending from the elongate shaft 110. The elongate shaft 110 is a dual lumen, tubular body including a proximal end portion 112 and a distal end portion 114, with the proximal end portion 112 and the distal end portion 114 defining a longitudinal axis "X." Each of the first and second tip segments 130, 150 has a respective proximal portion 132, 152 and a respective distal portion 134, 154. Proximal portions 132, 152 of the respective first and second tip segments 130, 150 are coupled to the distal end portion 114 of the elongate shaft 110. The first and second tip segments 130, 150 define respective first and second side openings 142, 162. As described in further detail below, each of the first and second tip segments 130, 150 is movable between a straight configuration, in which the respective tip segment 130, 150 is substantially parallel to the longitudinal axis "X," and a curved configuration, in which each tip segment 130, 150 has a concave portion with respect to the longitudinal axis "X" and the side openings 142, 162 face each other along the concave portions.

Figures 1, 2, 3:
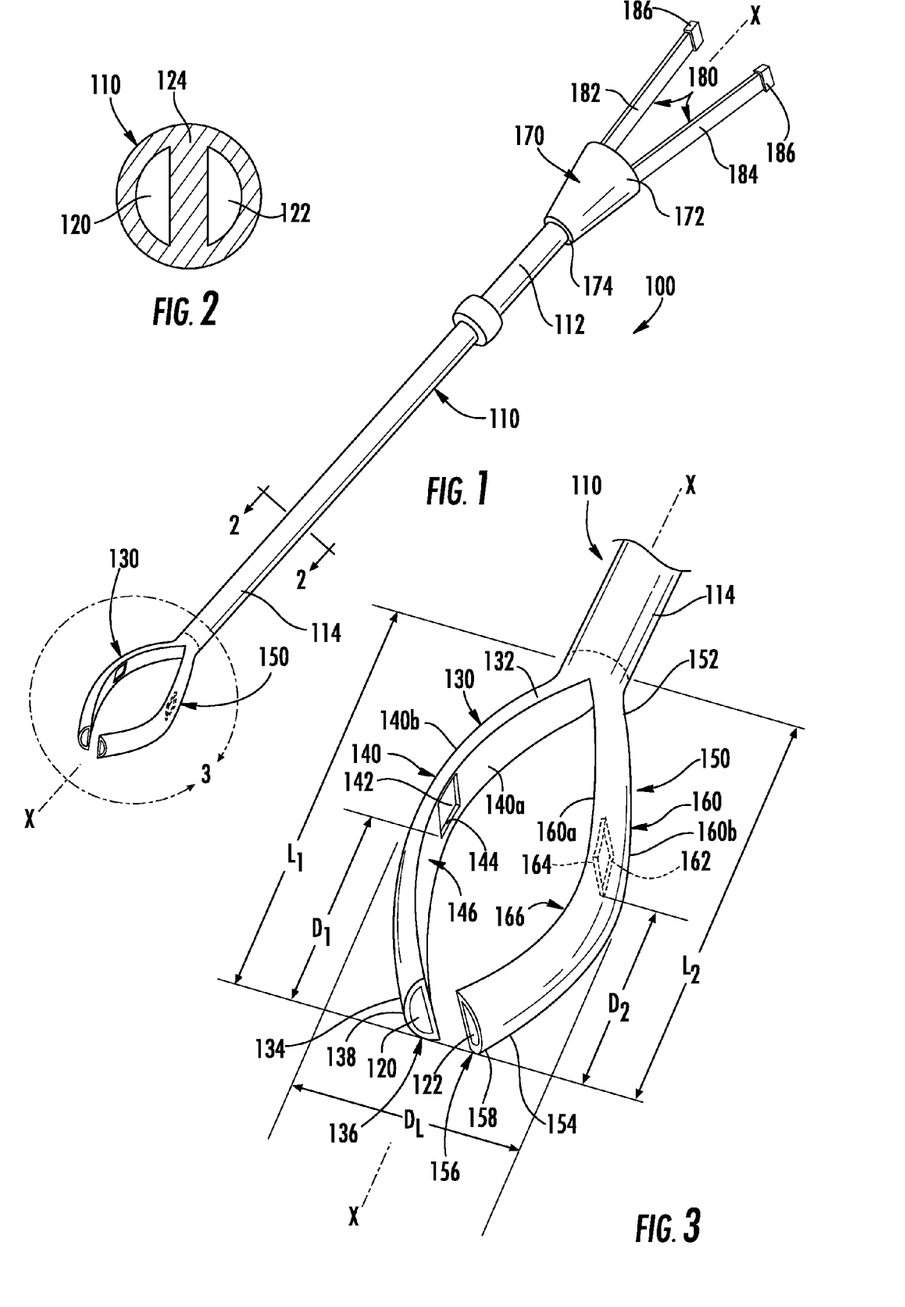
FIG. 1 is a perspective view of a catheter including first and second tip segments in a curved configuration.
FIG. 2 is a cross-sectional view of an elongate shaft of the catheter of FIG. 1, taken along line 2-2 of FIG. 1.
FIG. 3 is an enlarged, perspective view of a portion of the elongate shaft and the first and second tip segments of the catheter of FIG. 1, shown along the area of detail 3 identified in FIG. 1.
Figure 4:
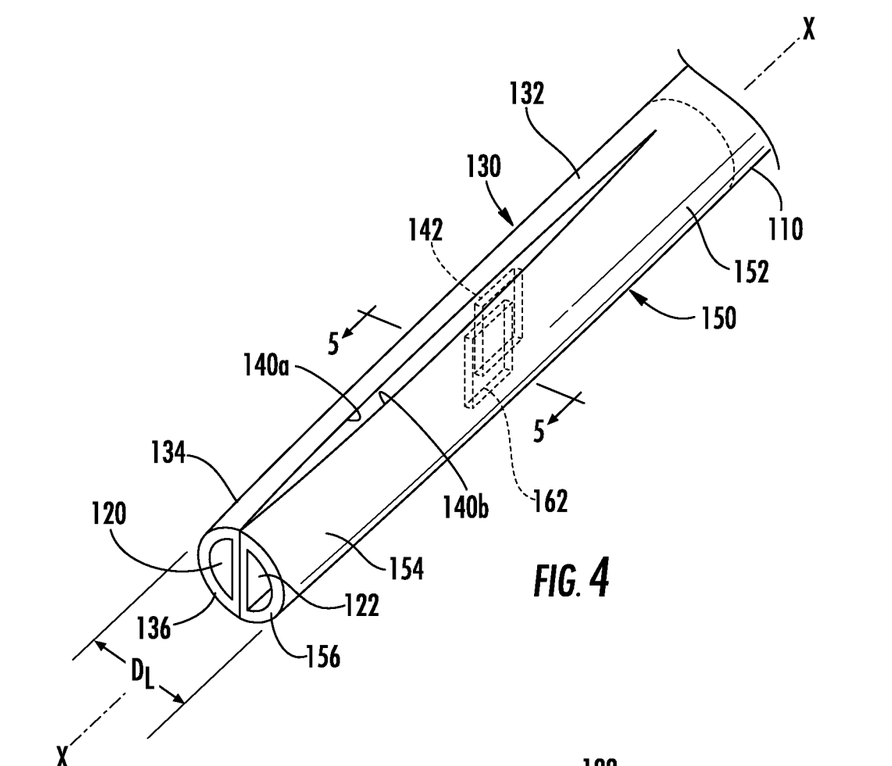
FIG. 4 is an enlarged, perspective view of a portion of the elongate shaft and the first and second tip segments of the catheter of FIG. 1, shown along the area of detail 3 identified in FIG. 1, with the first and second tip segments shown in a straight configuration.

In use, as also described in further detail below, the first and second tip segments 130, 150 are held in a straight configuration shown in FIG. 4 (e.g., through pressure exerted by a sheath (not shown) disposed over the first and second tip segments 130, 150). Once the first and second tip segments 130, 150 are in place within the vasculature of the subject, pressure on the first and second tip segments 130, 150 is removed (e.g., by withdrawal of the sheath) such that the first and second tip segments 130, 150 assume a curved configuration, shown in FIGS. 1 and 3, relative to one another. As shown in FIGS. 1 and 3, the first and second side openings 142, 162 may be located at an inner side of the respective tip segment 130, 150. As compared to catheters defining side openings on an outwardly facing surface, the inner facing relationship of the first and second side openings 142, 162 along the concave portion of the first and second tip segments 130, 150 can reduce the likelihood of positional occlusion of the first and second side openings 142, 162.

The elongate shaft 110 is at least partially flexible and can be straight or have a pre-curved configuration in the absence of an external stressor (e.g., to conform to a body cavity or body vessel in which the elongate shaft 110 is to be positioned). The elongate shaft 110 can be at least partially formed of, for example, biocompatible silicone and/or thermoplastic polyurethane. Additionally or alternatively, the elongate shaft 110 can include reinforcing material and/or additives to achieve, for example, column strength suitable for delivery of the elongate shaft 110 through the vasculature and to a treatment site of a subject.

The first and second tip segments 130, 150 each extend distally from the distal end portion 114 of the elongate shaft 110. The distal portion 134 of the first tip segment 130 can be adjacent (e.g., within about 3 mm of each other) the distal portion 154 of the second tip segment 150 in the straight configuration and in the curved configuration. For example, the length "$L_1$" of the first tip segment 130 can be substantially equal to the length "$L_2$" of the second tip segment 150. The distal portions 134, 154 of the first and second tip segments 130, 150 can, additionally or alternatively, be coterminous with one another in both the straight and curved configurations. The proximity of the distal portions 134, 154 of the first and second tip segments 130, 150 in the straight and curved configurations can facilitate placement of the respective distal portions 134, 154 at a desired location within the vasculature of a subject. For example, the position of the first and second tip segments 130, 150 in the curved configuration can be determined from the position of the first and second tip segments 130, 150 in the straight configuration used for delivery of the catheter 100.

In some embodiments, the respective lengths "$L_1$," "$L_2$" of the first and second tip segments 130, 150 is about 1 cm to about 4 cm. As compared to tip segments having shorter lengths, the first and second tip segments 130, 150 having these lengths can assume a curved configuration with a reduced likelihood of kinking or otherwise deforming. Additionally or alternatively, as compared to segments having longer lengths, the first and second tip segments 130, 150 having these lengths can have a substantially uniform radius of curvature in the curved configuration, which can facilitate manufacturing, while having an outer extent in the curved configuration that is suitable for placement in the vasculature of the subject as part of a hemodialysis treatment.

The first and second tip segments 130, 150 have substantially the same shape as each other and are symmetrical to one another, in both the straight and curved configurations, about at least one plane bisecting the elongate shaft 110 and including the longitudinal axis "X." As compared to catheters including asymmetric tip segments, it should be appreciated that such symmetry of the first and second tip segments 130, 150 can reduce the impact on flow performance associated with reversal of flow through the catheter 100. For example, in the presence of an occlusion, the flow through the first and second tip segments 130, 150 can be reversed to clear the occlusion, and the recirculation rate through the tip segments 130, 150 can remain below about 10% (e.g., below about 5%).

Each of the first and second tip segments 130, 150 defines a respective single lumen extending from the respective proximal portion 132, 152 to the respective distal portion 134, 154 of each of the first and second tip segments 130, 150. The proximal portions 132, 152 of the respective first and second tip segments 130, 150 are fixedly coupled to the distal end portion 114 of the elongate shaft 110 such that the elongate shaft 110 is in fluid communication with each of the first and second tip segments 130, 150. As shown in FIGS. 1 and 3, distal ends of the first and second side tip segments 130, 150 may not be connected to each other and may instead be movable relative to each other. Together, the elongate shaft 110 and the first and second tip segments 130, 150 define respective first and second lumens 120, 122 separated from fluid communication with each other. Each of the first and second lumens 120, 122 is in fluid communication with a respective side opening 142, 162 defined by the respective first and second tip segments 130, 150. The first and second lumens 120, 122 extend along the entire length of the elongate shaft 110 and the respective first and second tip segments 130, 150.

In certain embodiments, the first and second lumens 120, 122 are symmetrical to one another. As compared to catheters with asymmetric first and second lumens 120, 122, symmetric first and second lumens 120, 122 can reduce complexity associated with the formation of the catheter 100. Additionally or alternatively, symmetry of the first and second lumens 120, 122 can facilitate flow reversal through the catheter 100 with little to no impact on flow performance (e.g., recirculation) of the catheter 100.

The elongate shaft 110 includes a septum 124 disposed between the first and second lumens 120, 122 to separate the portions of the first and second lumens 120, 122 disposed within the elongate shaft 110 from fluid communication with one another. The septum 124 can extend from the proximal end portion 112 to the distal end portion 114 of the elongate shaft 110 such that the elongate shaft can be formed, for example, as an extrusion. In such embodiments, the first and second lumens 120, 122 extend from the proximal portion 112 of the elongate shaft 110, such that the first and second lumens 120, 122 are in fluid communication with the first and second extension tubes 182, 184, respectively, to the distal portions 134, 154 of the first and second tip segments 130, 150, such that the first and second lumens 120, 122 are in fluid communication with a body cavity or vessel in which the first and second tip segments 130, 150 are positioned.

The septum 124 can be useful as a point of attachment of the first and second tip segments 130, 150 to the distal end portion 114 of the elongate shaft 110. For example, the septum 124 can act as an alignment feature for aligning the first and second tip segments 130, 150 to the distal end portion 114. Additionally or alternatively, the first and second tip segments 130, 150 can be bonded (e.g., thermally, mechanically, and/or chemically) to the septum 124. In some embodiments, the septum 124 can have a thickness larger than (e.g., 2X) the wall thickness of the elongate shaft 110. As compared to an elongate shaft having a thinner septum, the larger thickness of the septum 124 can facilitate securement of the first and second tip segments 130, 150 to the septum 124 along the distal end portion 114 of the elongate shaft 110. The cross-sectional area, defined along a plane orthogonal to the longitudinal axis "X," of each of the first and second lumens 120, 122 is substantially constant along the entire length extending from the proximal end portion 112 of the elongate shaft 110 to the distal portions 134, 154 of the first and second tip segments 130, 150. As compared to catheters with non-uniform cross-sectional area of lumens, such substantially constant cross-sectional areas can, for example, reduce disruption in fluid flow at the point of connection between the elongate shaft 110 and the first and second tip segments 130, 150.

Each of the first and second lumens 120, 122 can have a substantially D-shaped cross-section in a plane orthogonal to the longitudinal axis "X." This substantially D-shaped cross-section of the first and second lumens 120, 122 can extend from the proximal end portion 112 of the elongate shaft 110 to the distal portion 134, 154 of each respective tip segment 130, 150. As compared to other configurations, the substantially D-shaped cross-section of the first and second lumens 120, 122 can facilitate the passage of a large volume of fluid through the first and second lumens 120, 122 while the overall shape of the elongate shaft 110 and the first and second tip segments 130, 150 in the straight configuration is maintained within a size envelope suitable for delivery of the catheter 100.

Figure 5:
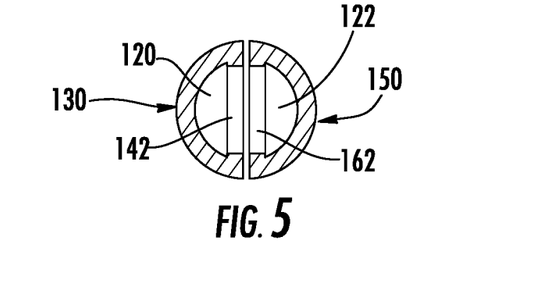
FIG. 5 is a cross-sectional view of the first and second tip segments of FIG. 4, taken along line 5-5 of FIG. 4.

Each of the first and second tip segments 130, 150 has a D-shaped outer surface 140, 160 including an inner, flat side 140a, 160a and an outer, rounded side 140b, 160b. The flat side 140a, 160a of each of the first and second tip segments 130, 150 faces the flat side of the other tip segment such that the overall outer circumference of the first and second tip segments 130, 150 in the straight configuration is substantially circular. As compared to catheters with non-circular profiles, the substantially circular profile of the first and second tip segments 130, 150 in the straight configuration can facilitate, for example, sheathing the catheter 100 for delivery through the vasculature of the subject. Additionally or alternatively, the overall outer circumference of the first and second tip segments 130, 150 in the straight configuration is substantially the same as the overall outer circumference of the elongate shaft 110 which can, for example, result an in atraumatic profile.

The flat side 140a, 160a of each of the first and second tip segments 130, 150 defines a respective one of the side openings 142, 162, with each side opening 142, 162 in fluid communication with a respective one of the first and second lumens 120, 122. The side openings 142, 162 may be substantially opposed to one another and, additionally or alternatively, may be identical in shape to one another. As compared to configuration in which side openings are asymmetrical, the symmetrical configuration of the side openings 142, 162 can facilitate flow reversal through the catheter 100 with little to no impact on flow performance. Each side opening 142, 162 may define a cross-sectional open area greater than or substantially similar to the cross-sectional area transverse to a flow path of a respective one of the first and second lumens 120, 122. Side openings 142, 162 with a cross-sectional open area greater than or substantially similar to a cross-sectional area of the respective first and second lumens 120, 122 can reduce the likelihood that the side openings 142, 162 will act as flow restrictions which, in certain instances, can promote lower shear rates and laminar flow of blood moving through the side openings 142, 162 and, thus, reduce the likelihood of thrombus formation.

Additionally or alternatively, edges 144, 164 of the side openings 142, 162 may be contoured (e.g., devoid of sharp edges) to reduce further shear stress and to facilitate laminar flow of blood through the side openings 142, 162 and to reduce the potential for formation of thrombus adjacent the side openings 142, 162. For example, the side openings 142, 162 can be laser cut to have contoured edges. Additionally or alternatively, the first and/or second tip segments 130, 150 can be molded to have contoured edges. As yet another additional or alternative example, the first and/or second tip segments 130, 150 can be treated via solvent vapor exposure to break sharp edges. The first and second tip segments 130, 150 are biased toward the curved configuration. As used herein, biased in the curved configuration will be understood to mean that, in the absence of external pressure on the first and second tip segments 130, 150, the first and second tip segments 130, 150 are each curved relative to the longitudinal axis "X." In the curved configuration, a portion of each of the flat sides 140a, 160a of the first and second tip segments 130, 150 are spaced apart and define concave portions 146, 166 with respect to the longitudinal axis "X." The concave portions 146, 166 provide lateral spacing of the side openings 142, 162 relative to one another while the side openings 142, 162 are oriented toward a center of a vessel wall of the subject. As compared to catheters defining side openings oriented away from one another and toward a vessel wall, the concave portions 146, 166 can, for example, reduce the likelihood of positional occlusion of the side openings 142, 162.

The maximum lateral distance "$D_L$" between the outer surfaces 140, 160 of the first and second tip segments 130, 150 in the curved configuration may be about 25 mm to about 30 mm. It should be appreciated that, in use, the actual lateral spacing between the outer surfaces 140, 160 of the first and second tip segments 130, 150 may be less than the maximum lateral distance "$D_L$" as a result of the outer surfaces 140, 160 of the first and second tip segments 130, 150 engaging with a vessel wall of the subject.

In some embodiments, the distal portions 134, 154 of the first and second tip segments 130, 150 define respective tip openings 136, 156 in fluid communication with a respective one of the first and second lumens 120, 122. Each of the tip openings 136, 156 may define a cross-sectional area substantially similar in size to a cross-sectional area of a respective one of the first and second lumens 120, 122 in a plane orthogonal to the longitudinal axis "X." Similarity in size of the tip openings 136, 156 and the first and second lumens 120, 122 can, for example, promote laminar flow through the first and second lumens 120, 122, reduce shear stress, and/or reduce the likelihood of thrombus formation. Additionally or alternatively, the tip openings 136, 156 may define a cross-sectional area substantially similar to (e.g., equal to) the cross-sectional area of each respective side opening 142, 162. The similarity in size between the tip openings 136, 156 and the respective side openings 142, 162 can, in certain instances, facilitate redirection of flow through an unblocked opening with little to no impact on overall flow performance of the catheter 100 in the event of positional occlusion of another opening in fluid communication with the respective lumen 120, 122. For example, in the event of positional occlusion of the tip opening 136, flow can exit the first lumen 120 through the respective side opening 142 until the positional occlusion can be addressed (e.g., through reversal of flow through the catheter 100).

Edges 138, 158 of the tip openings 136, 156 may be contoured (e.g., devoid of sharp edges), for example, to reduce shear stress and/or to facilitate laminar flow of blood through the tip openings 136, 156 and/or to reduce the potential for formation of thrombi adjacent the tip openings 136, 156. The tip openings 136, 156 can be laser cut to have contoured edges. Additionally or alternatively, the first and/ or second tip segments 130, 150 can be molded to have contoured edges. As yet another additional or alternative example, the first and/or second tip segments 130, 150 can be treated via solvent vapor exposure to break sharp edges In embodiments including the tip openings 136, 156, the side opening 142 of the first tip segment 130 is spaced a distance "$D_1$" from the tip opening 136, and the side opening 162 of the second tip segment 150 is spaced a distance "$D_2$" from the tip opening 156. The distances "$D_1$" and "$D_2$" may each be about 1 cm to about 4 cm. The distances "$D_1$," "$D_2$" may be, for example, about half the length "$L_1$," "$L_2$" of the respective one of the first and second tip segments 130, 150 which, as compared to positioning the side openings at other lengths along the first and second tip segments 130, 150, maximizes lateral spacing of the first and second side openings 142, 162 relative to one another when the first and second tip segments 130, 150 are in a curved configuration having a substantially constant radius of curvature. It should be appreciated that the lateral spacing of the first and second side openings 142, 162 can impact the flow characteristics through the catheter 100. For example, maximizing the lateral spacing between the first and second side openings 142, 162 can reduce the likelihood of recirculation of treated blood back into the catheter 100. In certain embodiments, the distance "$D_1$" is substantially equal to the distance "$D_2$."

The catheter hub 170 is dimensioned for manual engagement by a clinician and includes a proximal housing section 172 adjacent first and second extension tubes 182, 184 of the extension tube assembly 180, and a distal housing section 174 adjacent the elongate shaft 110. The proximal housing section 172 is attachable to the first and second extension tubes 182, 184, and the distal housing section 174 is attachable to the elongate shaft 110. Through these connections, the first and second extension tubes 182, 184 are in fluid communication with the respective first and second lumens 120, 122 which, in turn, are in fluid communication with a body cavity or vessel in which the first and second tip segments 130, 150 are positioned.

Each of the first and second extension tubes 182, 184 may include a respective luer adapter 186 at its free end for connection to inflow and outflow ports of a treatment device. Additionally or alternatively, a clamp (not shown) may be mounted about each of the first and second extension tubes 182, 184 to control fluid flow.

In an exemplary method of use, the first and second tip segments 130, 150 are moved from the curved configuration to the straight configuration in which the tip segments 130, 150 are substantially parallel to the longitudinal axis "X" of the elongate body 110, with the flat sides 140a, 160a of the first and second tip segments 130, 150 adjacent one another (e.g., touching one other). The first and second tip segments 130, 150 can be moved from the curved configuration to the straight configuration by squeezing the first and second tip segments 130, 150 together towards the longitudinal axis "X" during insertion into a target vessel, such as during placement within an introducer or sheath positioned within a vessel or body cavity of a subject.

After the first and second tip segments 130, 150 have been positioned adjacent or within a treatment site, the introducer or sheath is removed to allow bias of the first and second tip segments 130, 150 to return the first and second tip segments 130, 150 to the opposed curved configuration. In this opposed curved configuration, the first and second side openings 142, 162 are laterally spaced relative to one another and face each other within the vessel of the subject. In embodiments including the first and second tip openings 136, 156, at least a portion of each of the first and second tip openings 136, 156 face in a distal direction within the vessel or body cavity.

The first and second extension tubes 182, 184 are coupled to inflow and outflow ports of an extracorporeal treatment device (e.g., a hemodialysis machine), and the treatment device is activated. Blood is drawn from the vessel of the subject, through one of the side openings 142, 162, and directed through a respective one of the first and second lumens 120, 122 to the treatment device. The blood is treated by the treatment device, returned through the other of the first and second lumens 120, 122, and delivered from the respective one of the first and second tip segments 130, 150 into the vessel of the subject. For example, in embodiments in which the first and second tip segments 130, 150 define tip openings 136, 156, the pressure of the returning blood is sufficient to move the blood past the corresponding one of the side openings 142, 162 such that the blood is delivered to the vessel through the corresponding one of the tip openings 136, 156 in fluid communication with the respective lumen 120, 122 through which the blood is returned.

Thus, it should be appreciated that, in such embodiments, the side openings 142, 162 and the tip openings 136, 156 effectively stagger the intake and exhaust of blood to and from the catheter 100, with little to no treated blood being recirculated into the catheter 100.

In an exemplary method of manufacturing the catheter 100, the proximal ends 132, 152 of the first and second tip segments 130, 150 are pre-formed in the curved configuration and the proximal ends 132, 152 of the first and second tip segments 132, 152 are coupled to the distal end portion of the distal end portion 114 of the elongate shaft 110. For example, the proximal ends 132, 152 of the first and second tip segments 132, 152 can be melt formed with the distal end portion 114 of the elongate shaft 110. In some embodiments, melt forming includes the use of shrink wrapping and/or welding. The catheter hub 170 can be secured to the elongate shaft 110 and/or the first and second extension tubes 182, 184 through one or more of the following: an interference or frictional fit, bonding, welding, and/or use of cements or adhesives.

While certain embodiments have been described, other embodiments are possible.

For example, while catheters have been described as having substantially D-shaped lumens, other configurations are additionally or alternatively possible. For example, the first and second lumens 120, 122 can be kidney-shaped, oblong-shaped, C-shaped, circular, pie-shaped, etc. Additionally or alternatively, the shape and/or cross-sectional area of the first and second lumens 120, 122 may be different from one another.

As another example, while catheters have been described as being biased in a curved configuration, other configurations are additionally or alternatively possible. For example, a catheter may be biased in a straight configuration and moved to a curved configuration through the exertion of an external force.

With reference to FIGS. 6-10, a catheter 100' includes an elongate shaft 110', first and second tip segments 130', 150' extending distally from the elongate shaft 110', a catheter hub 170' and extension tubes 182, 184 extending proximally from the elongate shaft 110', and a wire 190 coupled to and disposed between the first and second tip segments 130', 150'. The wire 190 extends through the elongate shaft 110' and the catheter hub 170', and terminates proximal of the catheter hub 170'. In use, as described in further detail below, the wire 190 is moved proximally and distally along a longitudinal axis "X'" defined by a proximal end portion 112' and a distal end portion 114' of the elongate shaft 110'. The movement of the wire 190 along the longitudinal axis "X'" moves the first and second tip segments 130', 150' between a straight configuration substantially parallel to the longitudinal axis "X'" and a curved configuration relative to the longitudinal axis "X'."

Figures 6, 7, 8, 9:
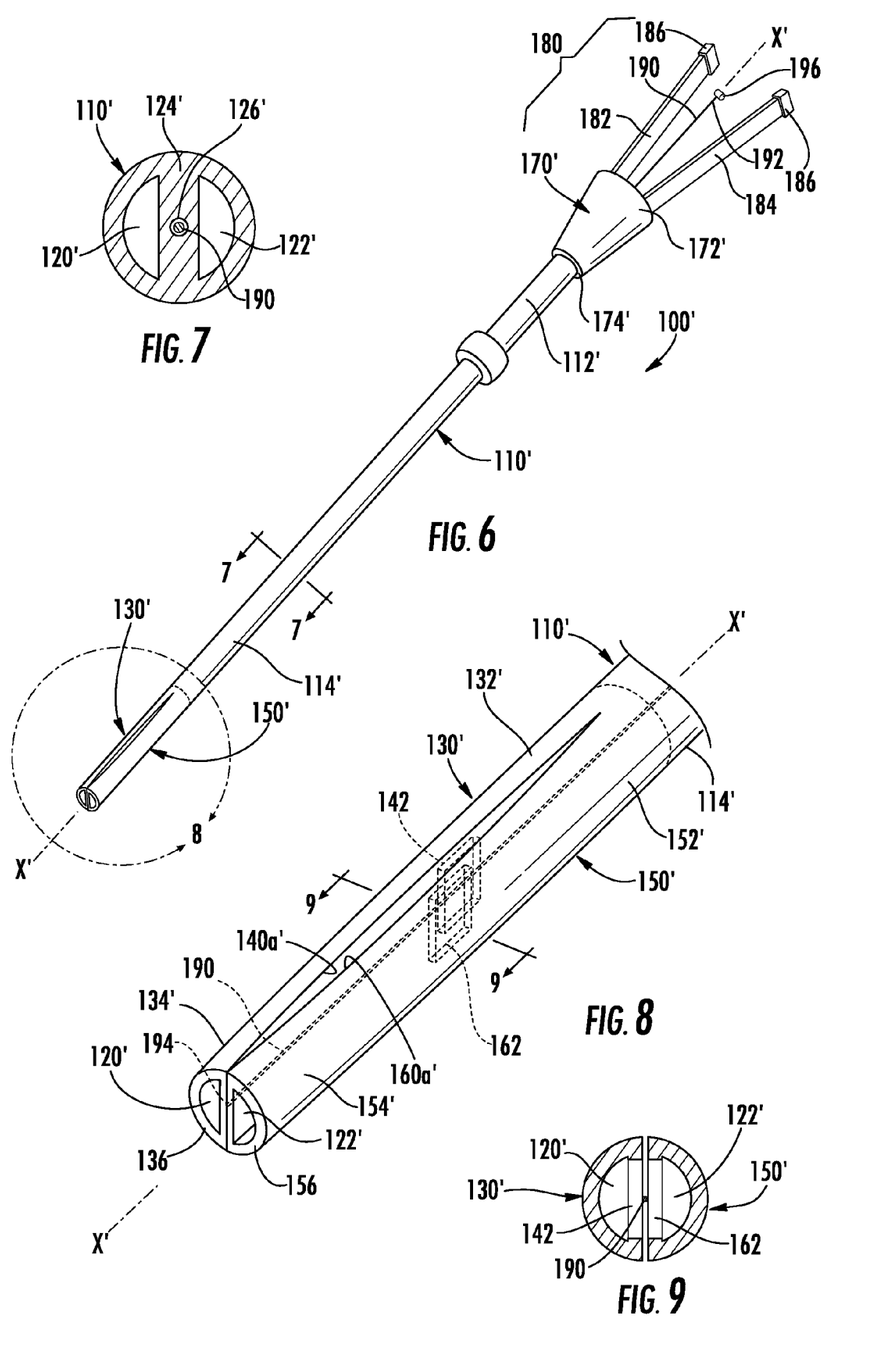
FIG. 6 is a perspective view of a catheter including first and second tip segments shown in a straight configuration.
FIG. 7 is a cross-sectional view of an elongate shaft of the catheter of FIG. 6, taken along line 7-7 of FIG. 6.
FIG. 8 is an enlarged, perspective view of a portion of the elongate shaft and the first and second tip segments of the catheter of FIG. 6, shown along the area of detail 8 identified in FIG. 6.
FIG. 9 is a cross-sectional view of the first and second tip segments of FIG. 8, taken along line 9-9 of FIG. 8.

The elongate shaft 110' has a triple lumen body extending from the proximal end portion 112' to the distal end portion 114', with each lumen extending substantially parallel to the longitudinal axis "X'." The distal end portion 114' of the elongate shaft 110' is fixedly coupled to proximal portions 132', 152' of the first and second tip segments 130', 150', with the elongate shaft 110' and the first and second tip segments 130', 150' defining respective first and second lumens 120', 122' separated from fluid communication with each other.

The wire 190 includes a proximal end portion 192 and a distal end portion 194 and is parallel to the longitudinal axis "X'." The distal end portion 194 of the wire 190 is fixedly attached to flat sides 140a', 160a' of the first and second tip segments 130', 150'. In some embodiments, the wire 190 is embedded into distal portions 134', 154' of the first and second tip segments 130', 150'. The wire 190 extends between the first and second tip segments 130', 150' and is at least partially disposed in a third lumen 126' defined within a septum 124' defining at least a portion of the first and second lumens 120', 122' of the elongate shaft 110'. The wire 190 further extends through the catheter hub 170' and out a proximal housing section 172' of the catheter hub 170', with the proximal end portion 192 of the wire 190 proximal to the catheter hub 170'. A collar 196 is disposed along the wire 190 and is movable along a length of the wire to lock the wire in place (e.g., through frictional engagement with the wire).

The tip segments 130', 150' are biased in a straight configuration in which the tip segments 130', 150' are substantially parallel to the longitudinal axis "X'" of the elongate body 110' such that, for example, the flat sides 140a', 160a' of the first and second tip segments 130', 150' are adjacent one another (e.g., touching one another) in the straight configuration.

Figure 10:
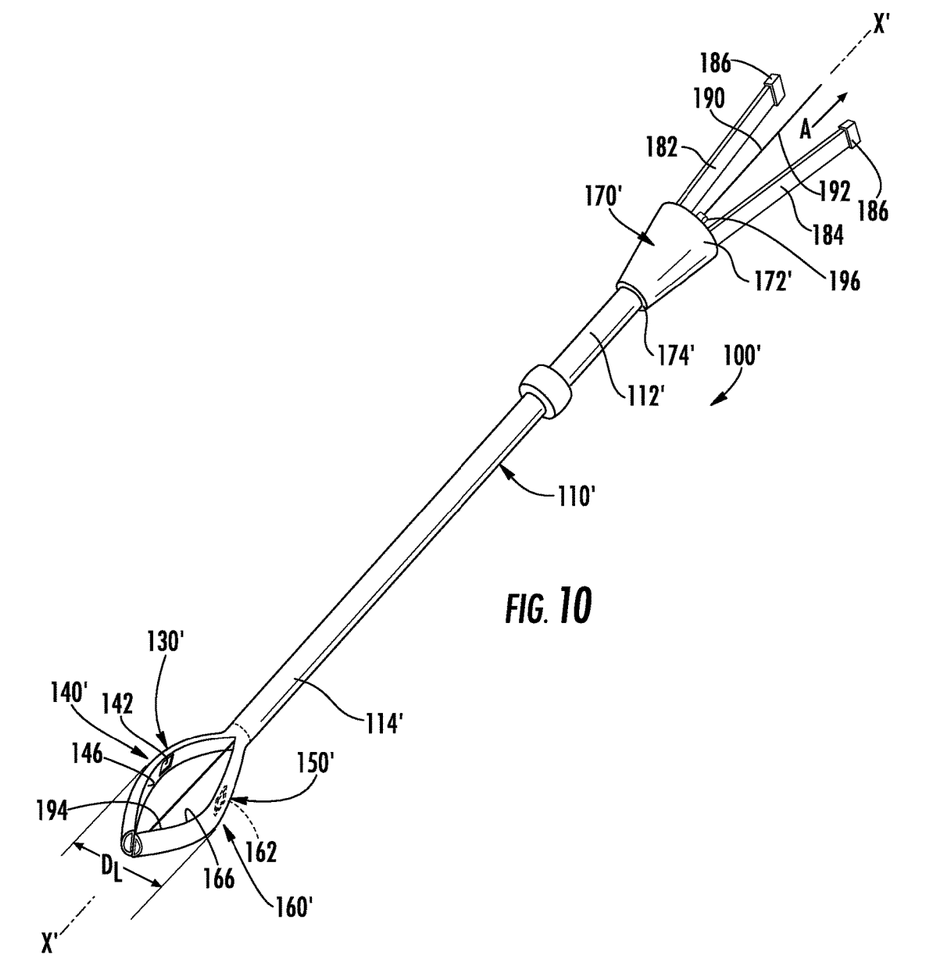
FIG. 10 is a perspective view of the catheter of FIG. 6, with the first and second tip segments shown in a curved configuration.

To move the first and second tip segments 130', 150' to the curved configuration, the proximal end portion 192 of the wire 190 is pulled proximally, in the direction of arrow "A," toward the proximal end portion 112' of the elongate shaft 110'. The first and second tip segments 130', 150' are sufficiently flexible such that movement of the wire 190 in the direction of arrow "A" exerts sufficient axial force on the first and second tip segments 130', 150' to cause an unattached portion of the first and second tip segments 130', 150' to diverge away from each other to define concave portions 146, 166 with respect to the longitudinal axis "X'" of the elongate shaft 110'.

With the first and second tip segments 130', 150' in the curved configuration, the collar 196 may be slid distally along the wire 190 until the collar 196 abuts the proximal housing section 172' of the catheter hub 170' to lock the wire 190 in place, thus locking the first and second tip segments 130', 150' in the curved configuration. In such embodiments, the maximum lateral distance between the outer surfaces 140', 160' of the first and second tip segments 130', 150' may be controlled, for example, by how far a clinician pulls the wire 190.

While the first and second tip segments 130', 150' have been described as being biased in a straight configuration, it should be appreciated that the first and second tip segments 130, 150 may be biased in the curved configuration. In such embodiments, the wire 190 is pushed distally towards the catheter hub 170' to move the first and second tip segments 130', 150' to the straight configuration, and the collar 196 may be utilized to lock the wire 190 in place, thus locking the first and second tip segments 130', 150' in the straight configuration for delivery through the vasculature of the subject.

As still another example, while catheters have been described in terms of medical catheters for the administration and/or withdrawal of fluids relative to the body of a subject, and more particularly, in terms of a hemodialysis catheter, other applications of such catheters are additionally or alternatively possible. For example, it should be appreciated that catheters of the present disclosure may be used in a range of catheter applications including, for example, surgical, diagnostic, and related treatments of diseases or body ailments of a subject. Additionally or alternatively, catheters of the present disclosure can be used for administration or withdrawal of fluids such as, for example, medication, saline, bodily fluids, blood, and/or urine.

A number of embodiments have been described. Nevertheless, it will be understood that various modifications may be made without departing from the spirit and scope of the disclosure. Accordingly, other embodiments are within the scope of the following claims.

What is claimed is:
1. A catheter comprising:
an elongate shaft having a proximal end portion and a distal end portion, the proximal and distal end portions defining a longitudinal axis, the elongate shaft defining a first shaft lumen and a second shaft lumen; and
first and second tip segments, the first shaft lumen of the elongate shaft together with the first tip segment defining a first catheter lumen, and the second shaft lumen of the elongate shaft together with the second tip segment defining a second catheter lumen separate from the first catheter lumen, each tip segment having a proximal portion, a distal portion, and a distal end, the proximal portion of each tip segment fixed relative to the distal end portion of the elongate shaft and the distal ends being movable relative to each other, each tip segment defining a side opening located at an inner side of the respective tip segment and in fluid communication with a respective one of the first and second catheter lumens,
wherein the tip segments are biased towards a curved configuration, in which each tip segment has a concave portion with respect to the longitudinal axis and the side openings face each other along the concave portions, and wherein each tip segment moves to a straight configuration, in which the respective tip segment is substantially parallel to the longitudinal axis, in response to an application of an external force to the respective tip segment, and moves from the straight configuration to the curved configuration in response to removal of the external force.

2. The catheter of claim 1, wherein the distal portion of the first tip segment is adjacent the distal portion of the second tip segment in the straight configuration and in the curved configuration.

3. The catheter of claim 1, wherein the distal portions of the first and second tip segments define respective tip openings in fluid communication with a respective one of the first and second catheter lumens.

4. The catheter of claim 3, wherein each tip opening defines a cross-sectional area substantially similar in size to a cross-sectional area transverse to a flow path of a respective one of the first and second catheter lumens.

5. The catheter of claim 3, wherein each tip opening defines a cross-sectional area substantially similar in size to a cross-sectional area defined by the respective side opening of the respective tip segment.

6. The catheter of claim 3, wherein, in the curved configuration, a distance between the side opening and the respective tip opening is at least about half the length of the respective tip segment.

7. The catheter of claim 3, wherein the side opening defined by the first tip segment is about 1 cm to about 4 cm from the respective tip opening defined by the first tip segment, and the side opening defined by the second tip segment is about 1 cm to about 4 cm from the respective tip opening defined by the second tip segment.

8. The catheter of claim 1, wherein the distal portions of the first and second tip segments are coterminous with one another in both the straight and curved configurations.

9. The catheter of claim 1, wherein the first tip segment and the second tip segment each has a length of about 1 cm to about 4 cm.

10. The catheter of claim 1 wherein, in the curved configuration, the maximum lateral distance between outer surfaces of the first and second tip segments is about 25 mm to about 30 mm.

11. The catheter of claim 1, wherein the first and second tip segments each have a D-shaped outer surface with a flat side of the D-shaped outer surface of each tip segment facing the flat side of the D-shaped outer surface of the other tip segment and the side opening of each tip segment defined along the flat side of the D-shaped outer surface of the respective tip segment.

12. The catheter of claim 1, wherein the first and second tip segments are symmetrical to one another, in both the straight and curved configurations, about at least one plane bisecting the elongate shaft and including the longitudinal axis.

13. The catheter of claim 1, wherein the first and second catheter lumens each have a D-shaped cross-section from the proximal end portion of the elongate shaft to the distal portion of the respective tip segment.

14. The catheter of claim 1, wherein the elongate shaft comprises a septum disposed between the first and second shaft lumens from the proximal end portion to the distal end portion of the elongate shaft.

15. The catheter of claim 1, wherein each of the side openings defines an open area substantially similar in size to a cross-sectional area transverse to a flow path of a respective one of the first and second catheter lumens.

16. The catheter of claim 1, further comprising one or more of an introducer or a sheath configured to transfer the external force to the respective tip segment.

17. The catheter of claim 1, further comprising a wire parallel to the longitudinal axis and coupled to the distal portions of the first and second tip segments, the wire movable in the direction of the longitudinal axis to move the first and second tip segments between the straight and curved configurations.

18. The catheter of claim 17, wherein the wire is movable toward the proximal end portion of the elongate shaft to move the first and second tip segments from the straight configuration to the curved configuration.

19. The catheter of claim 17, wherein the elongate shaft defines a third lumen and the wire is at least partially disposed in the third lumen.

20. The catheter of claim 17 further comprising a collar disposed along the wire, the collar movable along a length of the wire to lock the wire in place.

* * * * *